United States Patent
Abraham et al.

(10) Patent No.: US 12,406,341 B2
(45) Date of Patent: Sep. 2, 2025

(54) CORRECTING IMAGES FOR AN OPHTHALMIC IMAGING SYSTEM

(71) Applicant: ALCON INC., Fribourg (CH)

(72) Inventors: Mario Abraham, Burgthann (DE); Maik Lange, Ruckersdorf (DE)

(73) Assignee: ALCON INC., Fribourg (CH)

( * ) Notice: Subject to any disclaimer, the term of this patent is extended or adjusted under 35 U.S.C. 154(b) by 0 days.

(21) Appl. No.: 18/615,090

(22) Filed: Mar. 25, 2024

(65) Prior Publication Data
US 2024/0331113 A1 Oct. 3, 2024

Related U.S. Application Data

(60) Provisional application No. 63/492,656, filed on Mar. 28, 2023.

(51) Int. Cl.
*G06T 5/77* (2024.01)
*A61B 3/113* (2006.01)
*A61B 3/14* (2006.01)
*G06T 7/00* (2017.01)
*G06T 7/292* (2017.01)

(52) U.S. Cl.
CPC ........... *G06T 5/77* (2024.01); *A61B 3/113* (2013.01); *A61B 3/14* (2013.01); *G06T 7/0002* (2013.01); *G06T 7/292* (2017.01); *G06T 2207/10012* (2013.01); *G06T 2207/30041* (2013.01); *G06T 2207/30196* (2013.01)

(58) Field of Classification Search
None
See application file for complete search history.

(56) References Cited

U.S. PATENT DOCUMENTS

| | | | | |
|---|---|---|---|---|
| 9,172,871 B2 * | 10/2015 | Zhao | ............... | G06T 7/80 |
| 11,487,097 B1 * | 11/2022 | Park | ............... | G02B 21/16 |
| 11,792,538 B2 * | 10/2023 | Venkataraman | ....... | H04N 5/265 |
| | | | | 348/222.1 |
| 11,984,068 B2 * | 5/2024 | Lee | ............... | G09G 3/3208 |
| 2014/0232830 A1 * | 8/2014 | Ichige | ............... | H04N 13/239 |
| | | | | 348/47 |

(Continued)

FOREIGN PATENT DOCUMENTS

| AU | 2016201457 B2 * | 10/2017 | ............. A61B 3/117 |
|---|---|---|---|
| AU | 2016201457 A9 * | 11/2017 | ............. A61B 3/117 |

(Continued)

*Primary Examiner* — Ricky Chin

(57) ABSTRACT

In certain embodiments, an ophthalmic system images an eye region comprising at least one eye. The system includes a camera system and a computer. The camera system includes cameras that yield image portions of the eye region. Each camera is located at a position relative to the eye region and yields an image portion. The computer receives the image portions from the camera system. A first image portion is provided by a first camera, and a second image portion is provided by a second camera. The computer identifies identify target pixels of the first image portion, where the target pixels image a location of the eye region; determines image information of correction pixels of the second image portion, where the correction pixels image the same location of the eye region; and corrects the target pixels using the identified image information.

19 Claims, 5 Drawing Sheets

(56) References Cited

U.S. PATENT DOCUMENTS

| | | | | |
|---|---|---|---|---|
| 2014/0321771 | A1* | 10/2014 | Reinisch | G06T 11/60 |
| | | | | 382/284 |
| 2016/0263402 | A1* | 9/2016 | Zhang | A61N 5/1049 |
| 2017/0234976 | A1* | 8/2017 | Grauer | G01S 17/18 |
| | | | | 356/5.04 |
| 2018/0096487 | A1* | 4/2018 | Nash | H04N 23/45 |
| 2020/0139889 | A1* | 5/2020 | Christmann | B60R 1/002 |
| 2020/0150052 | A1* | 5/2020 | Lee | G01N 21/8903 |
| 2020/0201022 | A1* | 6/2020 | Shameli | G02B 23/243 |
| 2021/0243386 | A1* | 8/2021 | Park | H04N 5/2628 |
| 2021/0272302 | A1* | 9/2021 | Yang | G01B 11/22 |
| 2023/0230387 | A1* | 7/2023 | Herman | G06V 20/56 |
| | | | | 701/25 |
| 2023/0342894 | A1* | 10/2023 | Scharfenberger | G06T 3/4038 |
| 2024/0175244 | A1* | 5/2024 | Bhupatiraju | G06T 7/12 |
| 2024/0257691 | A1* | 8/2024 | Jeon | G09G 3/006 |
| 2024/0311964 | A1* | 9/2024 | Li | G06T 3/4053 |
| 2024/0331113 | A1* | 10/2024 | Abraham | G06T 5/77 |
| 2024/0331172 | A1* | 10/2024 | Abraham | A61B 3/14 |
| 2024/0412506 | A1* | 12/2024 | Kimita | G06V 10/993 |
| 2025/0017461 | A1* | 1/2025 | Abraham | A61B 3/145 |
| 2025/0037418 | A1* | 1/2025 | Momiyama | H04N 23/11 |
| 2025/0134374 | A1* | 5/2025 | Vaziri | A61B 5/1128 |

FOREIGN PATENT DOCUMENTS

| | | | | |
|---|---|---|---|---|
| CA | 2851687 A1 | * | 4/2013 | A61B 3/0025 |
| CA | 3236064 A1 | * | 6/2023 | A61B 3/12 |
| CN | 104768447 A | * | 7/2015 | A61B 3/0008 |
| CN | 113286078 A | * | 8/2021 | H04N 5/23222 |
| CN | 113592777 A | * | 11/2021 | G06T 5/50 |
| CN | 116148262 A | * | 5/2023 | G01N 21/8851 |
| EP | 4131182 A1 | * | 2/2023 | A61B 3/0008 |
| JP | 2023027405 A | * | 3/2023 | A61B 34/10 |

\* cited by examiner

CORRECTING IMAGES FOR AN OPHTHALMIC IMAGING SYSTEM

TECHNICAL FIELD

The present disclosure relates generally to ophthalmic imaging systems, and more particularly to correcting images for ophthalmic imaging systems.

BACKGROUND

Ophthalmic systems often provide an image of an eye for diagnosing or treating the eye. The eye is typically illuminated to generate the image. However, the illumination may cause undesired reflections that appear in the image.

BRIEF SUMMARY

In certain embodiments, an ophthalmic system images an eye region comprising at least one eye. The system includes a camera system, an illuminator, and a computer. The camera system includes cameras that yield image portions of the eye region. Each camera is located at a position relative to the eye region and yields an image portion. The illuminator is located at a position relative to the eye region and directs light towards the eye region. The computer receives the image portions from the camera system. A first image portion is provided by a first camera, and a second image portion is provided by a second camera. The computer identifies reflection pixels of the first image portion, where the reflection pixels image a reflection of light from the illuminator reflected by a location of the eye region; determines image information of correction pixels of the second image portion, where the correction pixels image the same location of the eye region; and corrects the reflection pixels using the identified image information to reduce the reflection.

Embodiments may include none, one, some, or all of the following features:

The cameras comprise stereoscopic cameras arranged symmetrically about the system axis of the camera system.

The computer identifies reflection pixels of the first image portion by detecting light saturated pixels as the reflection pixels.

The computer identifies reflection pixels of the first image portion by identifying the reflection pixels according to the position of the illuminator relative to the eye region and the position of the first camera relative to the eye region.

The computer identifies reflection pixels of the first image portion by: receiving eye tracking information describing movement of the eye; and identifying the reflection pixels according to the previous location of the reflection pixels and the movement of the eye.

The first camera is distinct from the second camera. The first camera is at a first position relative to the eye region, and the second camera is at a second position relative to the eye region distinct from the first position.

The first camera is the same as the second camera, and the second image portion provided prior to the first image portion.

The second image portion comprises default eye image information.

The computer corrects the reflection pixels using the identified image information by replacing the reflection pixels with the correction pixels.

The computer corrects the reflection pixels using the identified image information by applying an averaging function to the reflection pixels and the correction pixels.

The computer corrects the reflection pixels using the identified image information by: generating a correction overlay using the correction pixels; and placing the correction overlay over the reflection pixels.

In certain embodiments, an ophthalmic system images an eye region comprising at least one eye. The system includes a camera system and a computer. The camera system includes cameras that yield image portions of the eye region. Each camera is located at a position relative to the eye region and yields an image portion. The computer receives the image portions from the camera system. A first image portion is provided by a first camera, and a second image portion is provided by a second camera. The computer identifies identify target pixels of the first image portion, where the target pixels image a location of the eye region; determines image information of correction pixels of the second image portion, where the correction pixels image the same location of the eye region; and corrects the target pixels using the identified image information.

Embodiments may include none, one, some, or all of the following features:

The cameras comprise stereoscopic cameras arranged symmetrically about the system axis of the camera system.

The computer identifies target pixels of the first image portion by detecting light saturated pixels as the reflection pixels.

The computer identifies target pixels of the first image portion by: receiving eye tracking information describing movement of the eye; and identifying the target pixels according to the previous location of the target pixels and the movement of the eye.

The first camera is distinct from the second camera. The first camera is at a first position relative to the eye region, and the second camera is at a second position relative to the eye region distinct from the first position.

The first camera is the same as the second camera, and the second image portion provided prior to the first image portion.

The second image portion comprises default eye image information.

The computer corrects the target pixels using the identified image information by replacing the target pixels with the correction pixels.

The computer corrects the target pixels using the identified image information by: applying an averaging function to the target pixels and the correction pixels.

The computer corrects the target pixels using the identified image information by: generating a correction overlay using the correction pixels; and placing the correction overlay over the target pixels.

BRIEF DESCRIPTION OF THE DRAWINGS

FIG. 4 shows image portions that are used to yield a corrected image, and FIG. 5 shows a flowchart of the method.

DESCRIPTION OF EXAMPLE EMBODIMENTS

Figure 1:
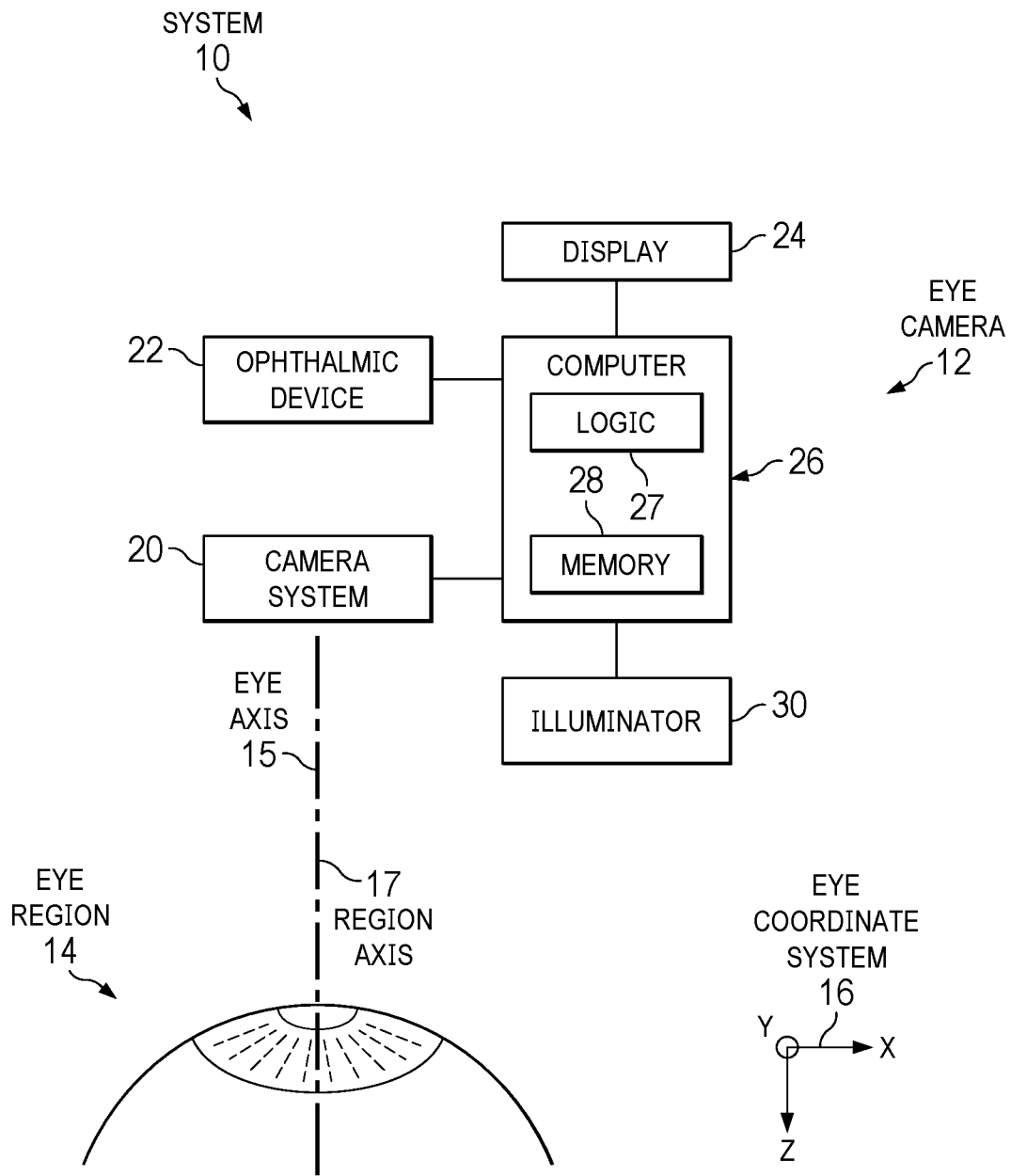
FIG. 1 illustrates an example of an ophthalmic system with an eye camera that provides images of an eye region, according to certain embodiments

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

According to a known technique for reducing problematic pixels of an image such as reflections, the illumination is polarized, and the polarized component is filtered out from the image. However, diffuse surfaces reflect polarized light in different directions, which can cause problems, e.g., the surface of an open LASIK flap can yield undesirable color shimmers. According to another known technique, reflections can be removed by interpolating information from adjacent pixels. However, known interpolation techniques may yield a less accurate image.

The ophthalmic imaging systems described herein have multiple cameras that provide images of the eye from different viewing directions to generate a digital image, such as an image in a microscope. The cameras have different lines of sight, so problematic pixels, such as reflections, appear at different locations in the images of the eye. If there is a reflection at a location of the eye in one image, image data from another image where the reflection is absent at that location may be used to correct the image. If there are locations where no image provides non-reflection image data, data from surrounding pixels may be interpolated to provide information for these locations.

FIG. 1 illustrates an example of an ophthalmic system 10 with an eye camera 12 that provides images of an eye region 14 (which may include one or both eyes of a patient), according to certain embodiments. For ease of explanation, certain eye features are used to define an example coordinate system 16 (x, y, z) of the eye. For example, the eye has a center (e.g., pupil center, apex, vertex) and an eye axis 15 (e.g., optical or pupillary axis) that can define the z-axis of eye coordinate system 16, which in turn defines an xy-plane of system 16. Eye region 14 has a region axis 17. If eye region 14 has one eye, region axis 17 may substantially coincide with eye axis 15. If eye region 14 has two eyes, region axis 17 may pass through a midpoint between the eyes.

As an overview of an example system, ophthalmic system 10 includes an eye camera 12, an ophthalmic device 22, a display 24, a computer 26 (which includes logic 27 and memory 28), and an illuminator 30, coupled as shown. Eye camera 12 includes a camera system 20 and computer 26, coupled as shown. As an overview of an example of operation, eye camera 12 provides images of an eye region 14. Camera system 20 has cameras that yield image portions of eye region 14. Each camera is located at a known position (e.g., a known location and/or orientation relative to each other and/or to eye region 14) and records at least a portion of eye region 14 to yield an image portion. Computer 26 receives the image portions from the camera system 20. Then, computer 26 identifies target pixels (e.g., reflection pixels) of one image portion at a location of the eye region, and determines image information of correction pixels of another image portion that image the same location of the eye region. Computer 26 corrects the target pixels using the identified image information. In some embodiments, if there are locations where no image provides usable (e.g., non-reflection) image data, data from surrounding pixels may be interpolated to provide information for these locations.

Any suitable target pixels may be corrected. For example, a target pixel may be a reflection pixel that images a reflection of light from the eye and is corrected to reduce the image of the reflection. As another example, a target pixel may be an obstructed pixel that images a location of the eye that has been blocked by, e.g., an instrument or a body part such as an eyelash.

Turning to the components, camera system 20 has a field of view (FOV) that covers eye region 14. The FOV has a known relationship to the coordinate system of camera system 20, which in certain embodiments has a known relationship to the coordinate system that ophthalmic device 22 uses to treat and/or diagnose an eye. In these embodiments, an eye tracker may track the position and movement of an eye by tracking the position and movement of the eye relative to the FOV. The eye tracking information may be used by ophthalmic device 22 to treat and/or diagnose the eye.

In the embodiments, camera system 20 includes cameras. For ease of explanation, the "position" of a camera relative to eye region 14 may describe the distance between the camera and eye region 14 and the direction of the camera axis relative to region axis 17. A camera detects light from an object and generates a signal in response to the light. The signal carries image data that can be used to generate the image of the eye. The image data are provided to computer 26 for eye tracking (and optionally other analysis) and may also be provided to display 24 to present the images of the eye. Examples of cameras include a charged-coupled device (CCD), video, complementary metal-oxide semiconductor (CMOS) sensor (e.g., active-pixel sensor (APS)), line sensor, and optical coherence tomography (OCT) camera.

A camera detects light of any suitable spectral range, e.g., a range of infrared (IR), ultraviolet (UV), and/or visible (VIS) wavelength light, where a range can include a portion or all of the wavelength. For example, a camera may detect visible light, infrared light, or other visible and infrared light from eye region 14 to yield an image portion. Certain cameras may capture features of the eye (e.g., pupil, iris, blood vessels, limbus, sclera, eyelashes, and/or eyelid) better than others. For example, an infrared camera generally provides more stable pupil tracking and better contrast for iris structures. Accordingly, an IR camera may be used to monitor lateral movement by tracking the pupil and/or cyclotorsion by tracking iris structures. As another example, a visible range camera yields better images of blood vessels, so a visible range camera may be used to monitor translation and/or rotational movement by tracking blood vessels.

A camera may record images at any suitable frequency or resolution. A higher speed camera may record images at greater than, e.g., 400 to 1500 frames per second, such as greater than 500, 750, or 1000 frames per second. A higher resolution camera may yield images with greater than, e.g., 4 to 24 megapixels, such as greater than 5, 10, 15, or 20 megapixels. In general, higher resolution images and higher speed image acquisition may provide more accurate tracking, but both features may require more computing time, so there may be a trade-off between resolution and speed.

Accordingly, the speed and/or resolution of a camera may be selected for particular purposes. In certain embodiments, a higher speed camera may track eye features that move faster and/or can be identified with lower resolution, and a higher resolution camera may be used to track eye features that require higher resolution for identification and/or move more slowly. For example, a lower resolution, higher speed camera may track the pupil (which does not require high resolution) to detect xy-movement. As another example, a higher resolution, lower speed camera may track blood vessels/iris structures to detect rotations, z-movement.

Ophthalmic device 22 may be a system that is used to diagnose and/or treat an eye. Examples include a refractive surgical system, a cataract system, a topographer, an OCT measuring device, and a wavefront measuring device. Display 24 provides images to the user of system 10. Examples of display 24 include a computer monitor, a 3D display, a projector/beamer, a TV monitor, binocular displays, glasses with monitors, a virtual reality display, an augmented reality display, and a mixed reality display.

Illuminator 30 directs light towards eye region 14 to illuminate the eye for imaging. An illuminator 30 may comprise one or more light sources, such as one or more of any of the following, a lamp, an LED (which may be white or monochrome, e.g., green, red, IR, or UV), a laser diode (with the same example colors as the LED), and/or a projected light pattern (e.g., dots, lines, or crosses). In certain embodiments, room illumination or sunlight may provide illumination.

Computer 26 controls components of system 10 (e.g., camera system 20, an ophthalmic device 22, a display 24, and/or light projector 30) to image an eye. In general, computer 16 receives the image portions from camera system 20 and corrects pixels of the image portions to yield an image of eye region 14. As an overview, computer 26 identifies target pixels, e.g., reflection pixels that image reflection of light in an image. Computer 26 determines image information of correction pixels from, e.g., another image, and corrects the target pixels using the image information from the correction pixels.

In embodiments that correct reflection pixels, the reflection pixels may be identified in any suitable manner. For example, computer 26 may use image processing to detect light saturated pixels at the reflection pixels. A light saturated pixel may be, e.g., a pixel with a greater than 90 percent of maximum level reading. As another example, computer 26 may calculate the location of the reflection pixels according to the position of illuminator 30 and the position of the camera that provided the image. The position of illuminator 30 provides the direction of the light rays incident on and reflected from the eye. The position of the camera provides the location of the eye where the camera received the reflected light. As another example, computer 26 may receive eye tracking information describing movement of the eye, and then calculate the location of the reflection pixels according to the previous location of the pixels and the movement of the eye. Since the reflection moves with the eye, the location of the reflection pixels can be determined from the previous location and the movement.

In the embodiments, computer 26 determines image information using correction pixels of a second image portion, where the correction pixels image the same location of the eye where the reflections appear in the first image. Image information may be determined in any suitable manner. For example, the image information may be determined from a second image portion provided by a different camera in a different position from the camera that provided the first image portion, e.g., stereoscopically arranged cameras. Since the cameras are in different positions, a reflection may appear at a location of the eye in one image, but the reflection may appear at different location of the eye in another image.

As another example, the image information may be determined from a second image portion provided by the same camera that provided the first image portion, where the camera generated the first and second image portions at different times. As another example, computer 26 may determine the image information from a second image portion that comprises default eye image information. Default eye image information may comprise, e.g., image data of a typical eye at the location. For example, if the correction pixels are for correcting pixels at the pupil, the default eye image information may comprise dark pixels.

In the embodiments, computer 26 uses the identified image information to reduce reflection in any suitable manner. For example, computer 26 may replace the reflection pixels with correction pixels. As another example, computer 26 may apply an averaging function to the reflection pixels and correction pixels. For example, the averaging function may weight the pixels equivalently or may give greater weight to pixels from, e.g., an image with higher quality. As another example, computer 26 may generate a correction overlay using the correction pixels, and place the correction overlay over the reflection pixels.

Figure 2:
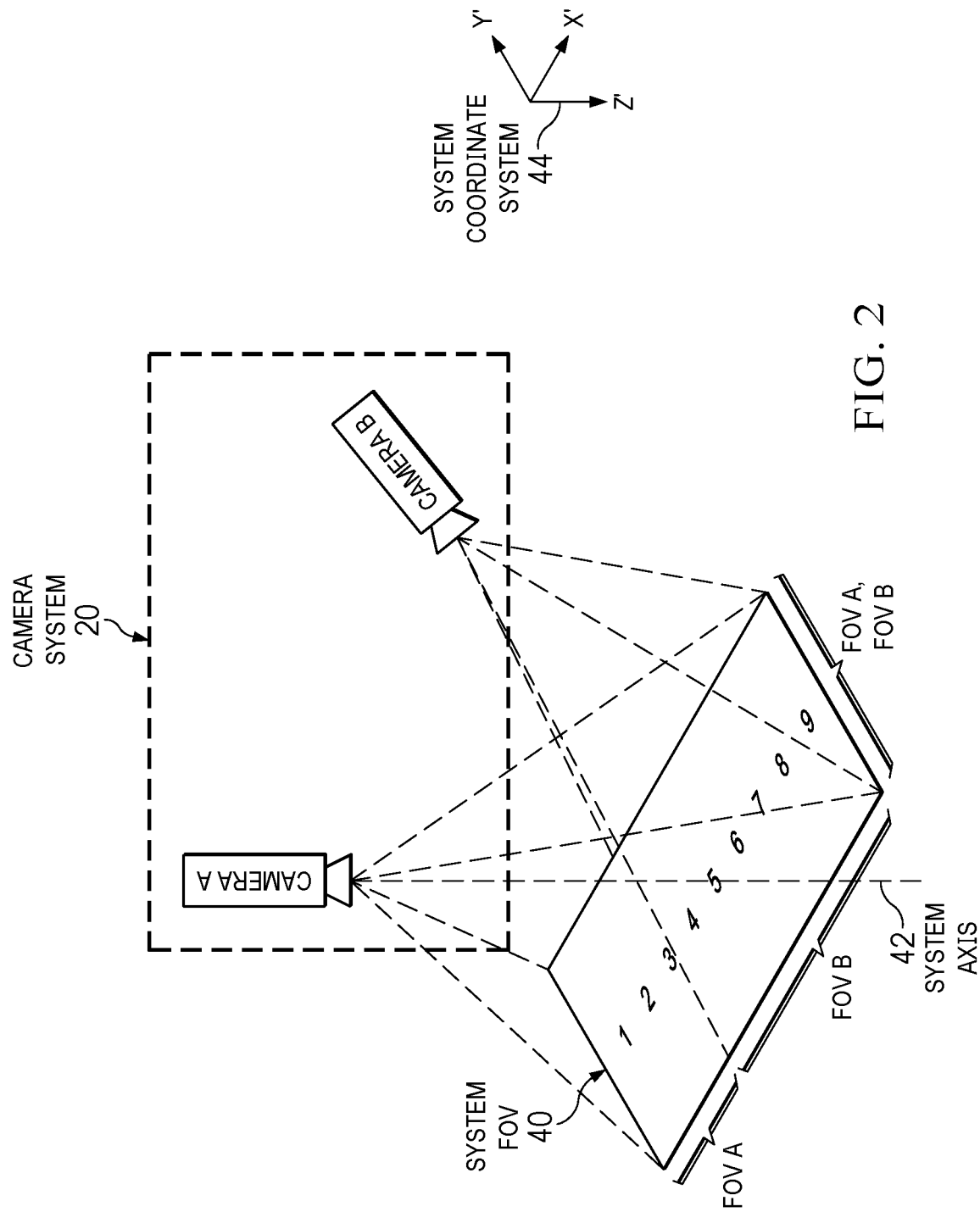
FIG. 2 illustrates an example of the field of view (FOV) of the camera system of FIG. 1, according to certain embodiments.

FIG. 2 illustrates an example of the field of view (FOV) 40 of camera system 20 of FIG. 1, according to certain embodiments. The cameras of camera system 20 may have any suitable arrangement. For example, Camera A and Camera A may be arranged mirror symmetrically about system axis 14, i.e., spatially separated with equal viewing angles on opposite sides of system axis 14. The images may be stereoscopically reconstructed to track the location and orientation of an eye in two or three dimensions. The greater the angle and/or distance between the cameras, the better the accuracy in the z-direction. This may facilitate positioning the head of the patient.

A camera of camera system 20 has a field of view (FOV) that detects light from eye region 14 to yield an image portion 45 of some or all of eye region 14. Different cameras can have different FOVs that detect light from different portions of eye region at different directions, and different FOVs may overlap. In certain embodiments, the combined FOVs from the cameras yield a system FOV 40. In general, more cameras at different positions (locations and orientations) may improve the detection of eye features and the accuracy of the tracking.

In the example, camera system 20 has a system FOV 40, a system axis 42, and a system coordinate system 44 (x', y', z'). System axis 42 may have any suitable position, e.g., axis 42 may be substantially orthogonal to system FOV 40 and may pass through the center of system FOV 40. System axis 42 and system coordinate system 44 (x', y', z') may be related in any suitable manner. In the example, system axis 42 defines the z'-axis of system coordinate system 44. In the example, system FOV 40 is generally planar and images the numbers 1 through 9. Camera system 20 includes Camera A with FOV A and Camera B with FOV B, where FOV A and FOV B extend partially or fully over system FOV 40. Camera A provides a first image portion taken with FOV A, and Camera B provides a second image portion taken with FOV B.

In certain embodiments, computer 26 aligns and combines image portions 45 to yield combined image 46. Image portions 45 may be aligned in any suitable manner. For example, each camera has a known position, such as a location (e.g., distance away from system FOV 40 and/or eye region 14), orientation (e.g., camera optical axis relative to system axis 42 and/or eye axis 15, or viewing angle), dimensions, and imaging properties. From this information, computer 26 can determine the positions of image portions 45 to align them within combined image 46. As another example, the cameras each generate an image of a calibration figure (e.g., a checkerboard), and the positions of the cameras are determined from the images. As yet another example, a user calibrates image portions 45 by manually aligning portions 45 when viewed through the cameras. Computer 26 records the positions of the aligned portions.

Figure 3A:
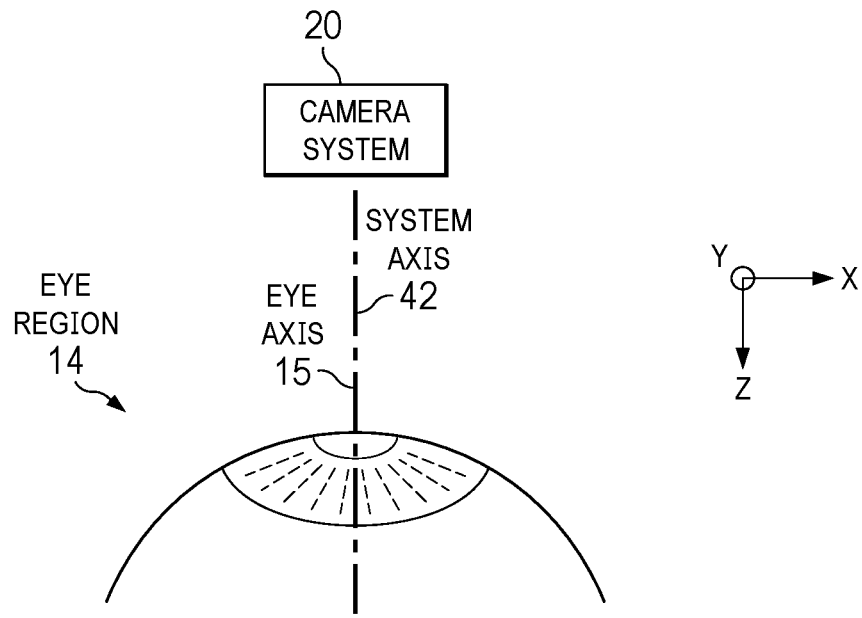
FIGS. 3A and 3B illustrate examples the camera system of FIG. 1 tracking eye regions, according to certain embodiments.
Figure 3B:
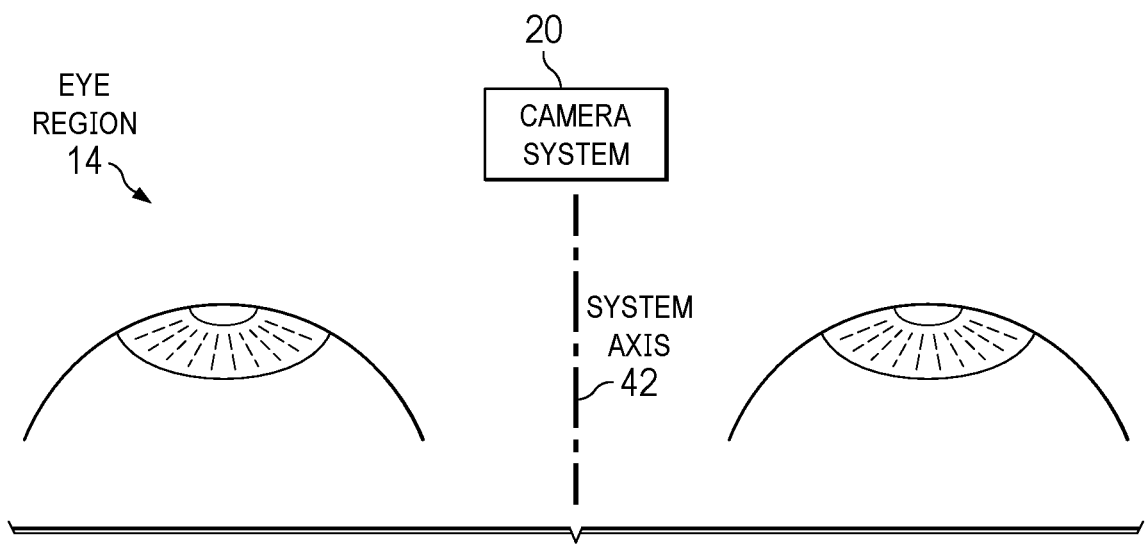

FIGS. 3A and 3B illustrate examples camera system 20 of FIG. 1 tracking eye regions 14, according to certain embodiments. In FIG. 3A, eye region 14 includes one eye. In the example, eye axis 15 of the eye may at first be substantially aligned with system axis 42 of camera system 20. As the eye moves relative to camera system 20, eye axis 15 moves relative to system axis 42.

In FIG. 3B, eye region 14 includes both eyes. System axis 42 of camera system 20 may be aligned in any suitable location, e.g., substantially aligned with the midpoint between the eyes. Camera system 20 includes cameras that image one or both eyes to yield a combined image that images both eyes simultaneously, so camera system 20 can track both eyes simultaneously and independently of one another. In certain embodiments, camera system 20 includes a pair of stereoscopic cameras that can each image both eyes to provide three-dimensional image information, including z-depth information for both eyes.

Figure 4:
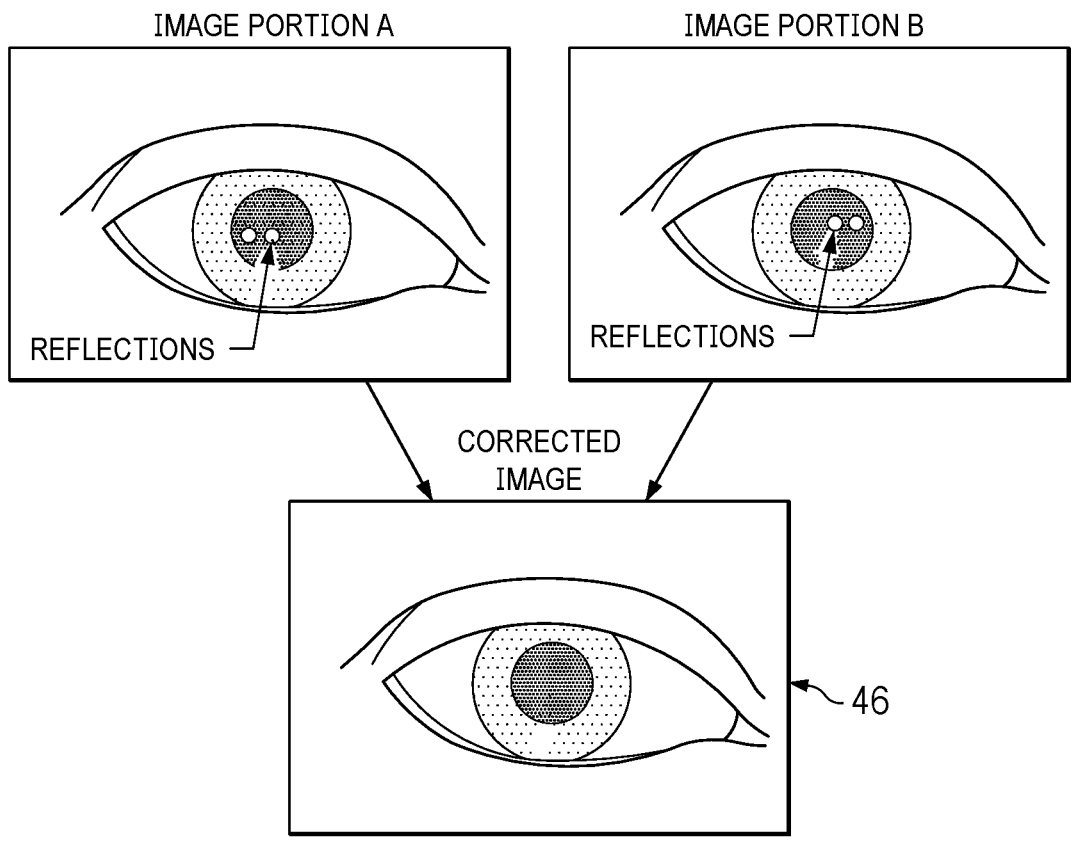
FIGS. 4 and 5 illustrate an example of a method for correcting pixels in an eye image, according to certain embodiments.
Figure 5:
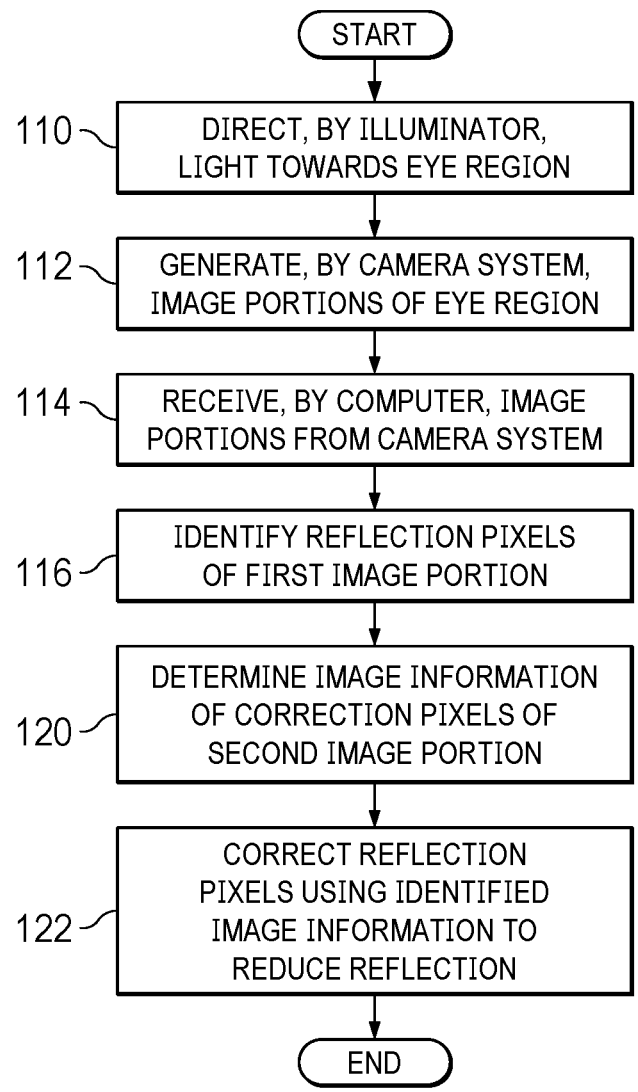

FIGS. 4 and 5 illustrate an example of a method for correcting pixels, such as reflection pixels, in an eye image, according to certain embodiments. FIG. 4 shows image portions A and B that are used to yield corrected image 46, and FIG. 5 shows a flowchart of the method. The method starts at step 110, where illuminator 30 directs light towards eye region 14. Camera system 20 generates image portions A and B of eye region 14 at step 112. Computer 26 receives image portions A and B from camera system 20 at step 114.

Computer 26 identifies reflection pixels of image portion A at step 116. The reflection pixels image the reflection of light at a particular location of eye region 14. Reflection pixels may be identified in any suitable manner. For example, computer 26 may detect light saturated pixels as reflection pixels. As another example, computer 26 may calculate the location of the reflection pixels according to the position of illuminator 30 and position of the camera that provided image portion A. As another example, computer 26 may receive eye tracking information describing movement of the eye, and then calculate the location of the reflection pixels according to the previous position of the pixels and the movement of the eye.

Computer 26 determines image information of correction pixels of image portion B that image the same location of the eye region at step 120. Image information may be determined in any suitable image portion B. For example, image portion B may be provided by a camera distinct from the camera that provided image portion A. As another example, image portion B may be provided by the same camera, but image portion B may have been taken before or after image portion A. As another example, image portion B may comprise default eye image information.

Computer 26 corrects the reflection pixels using the identified image information to reduce reflection at step 122. The reflection pixels may be corrected in any suitable manner. For example, computer 26 may replace the reflection pixels with correction pixels. As another example, computer 26 may apply an averaging function to the reflection pixels and correction pixels. As another example, computer 26 may generate a correction overlay using the correction pixels, and place the correction overlay onto the reflection pixels.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic system that images an eye region comprising at least one eye, comprising:
a camera system comprising a plurality of cameras configured to yield a plurality of image portions of the eye region, each camera located at a position relative to the eye region and configured to yield an image portion of the plurality of image portions;
an illuminator located at a position relative to the eye region and configured to direct light towards the eye region; and
a computer configured to:
receive the plurality of image portions from the camera system, the plurality of image portions comprising a first image portion and a second image portion, the first image portion provided by a first camera, the second image portion provided by a second camera;
identify one or more reflection pixels of the first image portion, the reflection pixels imaging a reflection of light from the illuminator reflected by a location of the eye region;
determine image information of one or more correction pixels of the second image portion, the correction pixels imaging the same location of the eye region; and
correct the reflection pixels using the identified image information to reduce the reflection by:
generating a correction overlay using the one or more correction pixels; and
placing the correction overlay over the one or more reflection pixels.

2. The ophthalmic system of claim 1, the plurality of cameras comprising a set of stereoscopic cameras arranged symmetrically about a system axis of the camera system.

3. The ophthalmic system of claim 1, the computer configured to identify one or more reflection pixels of the first image portion by:
detecting one or more light saturated pixels as the one or more reflection pixels.

4. The ophthalmic system of claim 1, the computer configured to identify one or more reflection pixels of the first image portion by:
identifying the one or more reflection pixels according to the position of the illuminator relative to the eye region and the position of the first camera relative to the eye region.

5. The ophthalmic system of claim 1, the computer configured to identify one or more reflection pixels of the first image portion by:
receiving eye tracking information describing movement of the eye; and
identifying the one or more reflection pixels according to a previous location of the one or more reflection pixels and the movement of the eye.

6. The ophthalmic system of claim 1, the first camera distinct from the second camera, the first camera at a first position relative to the eye region, the second camera at a second position relative to the eye region distinct from the first position.

7. The ophthalmic system of claim 1, the first camera the same as the second camera, the second image portion provided prior to the first image portion.

8. The ophthalmic system of claim 1, the second image portion comprising default eye image information.

9. The ophthalmic system of claim 1, the computer configured to correct the reflection pixels using the identified image information by:
replacing the one or more reflection pixels with the one or more correction pixels.

10. The ophthalmic system of claim 1, the computer configured to correct the reflection pixels using the identified image information by:
applying an averaging function to the one or more reflection pixels and the one or more correction pixels.

11. An ophthalmic system that images an eye region comprising at least one eye, comprising:
a camera system comprising a plurality of cameras configured to yield a plurality of image portions of the eye region, each camera located at a position relative to the eye region and configured to yield an image portion of the plurality of image portions; and
a computer configured to:
receive the plurality of image portions from the camera system, the plurality of image portions comprising a first image portion and a second image portion, the first image portion provided by a first camera, the second image portion provided by a second camera;
identify one or more target pixels of the first image portion, the target pixels imaging a location of the eye region;
determine image information of one or more correction pixels of the second image portion, the correction pixels imaging the same location of the eye region; and
correct the target pixels using the identified image information by:
generating a correction overlay using the one or more correction pixels; and
placing the correction overlay over the one or more target pixels.

12. The ophthalmic system of claim 11, the plurality of cameras comprising a set of stereoscopic cameras arranged symmetrically about a system axis of the camera system.

13. The ophthalmic system of claim 11, the computer configured to identify one or more target pixels of the first image portion by:
detecting one or more light saturated pixels as the one or more target pixels.

14. The ophthalmic system of claim 11, the computer configured to identify one or more target pixels of the first image portion by:
receiving eye tracking information describing movement of the eye; and
identifying the one or more target pixels according to a previous location of the one or more target pixels and the movement of the eye.

15. The ophthalmic system of claim 11, the first camera distinct from the second camera, the first camera at a first position relative to the eye region, the second camera at a second position relative to the eye region distinct from the first position.

16. The ophthalmic system of claim 11, the first camera the same as the second camera, the second image portion provided prior to the first image portion.

17. The ophthalmic system of claim 11, the second image portion comprising default eye image information.

18. The ophthalmic system of claim 11, the computer configured to correct the target pixels using the identified image information by:
replacing the one or more target pixels with the one or more correction pixels.

19. The ophthalmic system of claim 11, the computer configured to correct the target pixels using the identified image information by:

applying an averaging function to the one or more target pixels and the one or more correction pixels.

\* \* \* \* \*